United States Patent [19]

Yamamoto

[11] Patent Number: 4,681,582

[45] Date of Patent: Jul. 21, 1987

[54] DRUG ADMINISTERING APPARATUS

[75] Inventor: Yuichi Yamamoto, Fujinomiya, Japan

[73] Assignee: Terumo Kabushiki Kaisha, Tokyo, Japan

[21] Appl. No.: 743,412

[22] Filed: Jun. 11, 1985

[30] Foreign Application Priority Data

Jun. 13, 1984 [JP] Japan ............................ 59-121463/1

[51] Int. Cl.⁴ .............................................. A61K 9/22
[52] U.S. Cl. ...................................... 604/890; 604/84
[58] Field of Search ................. 604/890, 891, 892, 83, 604/84

[56] References Cited

U.S. PATENT DOCUMENTS

| | | | |
|---|---|---|---|
| 4,217,894 | 8/1980 | Franetzki | 604/84 |
| 4,431,428 | 2/1984 | Schmer | 604/890 |
| 4,479,796 | 10/1984 | Kallok | 604/84 |

*Primary Examiner*—John D. Yasko
*Attorney, Agent, or Firm*—Burns, Doane, Swecker & Mathis

[57] ABSTRACT

A drug administering apparatus includes a container with body fluid inlet and outlet ports which communicate with each other, and a liposome agent entrapping a drug therein. An insoluble substance is fixed inside the container and has the liposome agent such that the liposome agent can be brought into contact with the body fluid flowing in the container. The drug entrapped in the liposome is released into the body fluid flowing in the container.

17 Claims, 6 Drawing Figures

F I G. 5
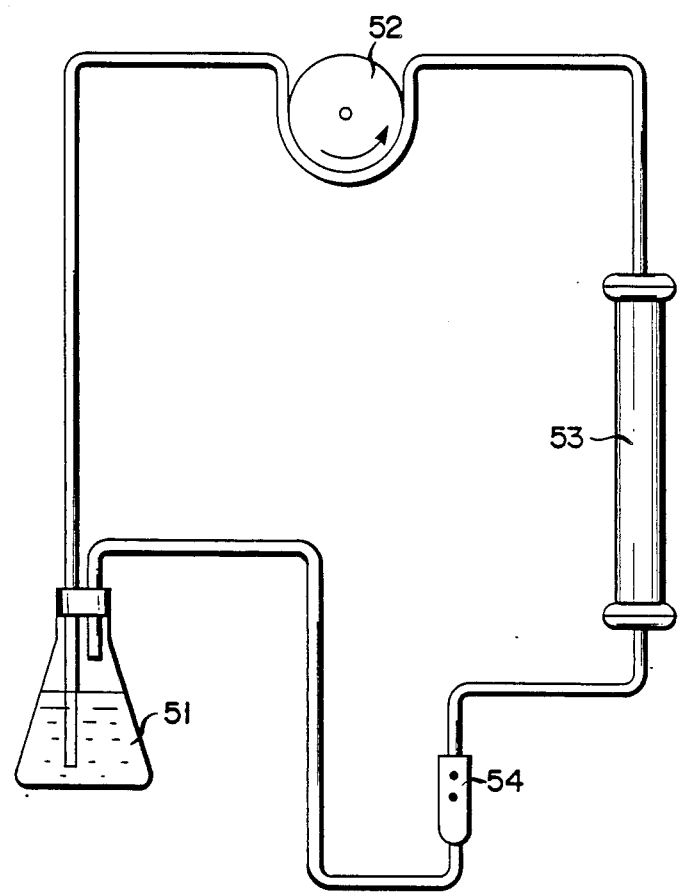

DRUG ADMINISTERING APPARATUS

BACKGROUND OF THE INVENTION

1. Field of the Invention

The present invention relates to a drug administering apparatus having an excellent sustained release property for a drug or liposome in which a liposome preparation or composition encapsulating therein a drug to be administered to a biological organism is immobilized in a polymeric substance fixed on a surface of an insoluble support.

2. Description of the Prior Art

Liposomes mainly consisting of phospholipids and various lipids as membrane constituting components have excellent biocompatibility and can be safely used for oral drugs, or parenteral drugs such as an injection solution or an ointment. Application of liposomes to targeting therapy is being studied due to their tendency to concentrate in the reticuloendothelial system and ability to pass through cerebral blood vessels. However, conventional liposomes have poor physical and chemical stability and short life in biological organisms; their membranes are easily damaged in vitro or in vivo and thereupon spontaneously release the drug.

General drugs upon being administered are absorbed from an administered portion of a human body and spread to the entire body through the blood and lympha. The drugs reach a diseased portion of the body through complex procedures. The effect of the drug is closely related to the drug concentration in blood. As can be seen from FIG. 1 (typical change in drug concentration in blood), how to maintain an effective drug concentration for a given therapy time is an important problem in economically performing therapy without causing side effects.

SUMMARY OF THE INVENTION

It is an object of the present invention to provide a drug administering apparatus which resolves the problem of easy damage to liposome membranes in vitro or in vivo, has an excellent sustained release property for a substance encapsulated (entrapped) in a liposome to be administered to a human body and also for the liposome itself, and can be used as an extracorporeal therapy column capable of holding a stable drug effect over a long period of time or as a bioagitator for activating cell function.

According to the present invention, there is provided a drug administering apparatus comprising:

a container with fluid inlet and outlet ports which communicate with each other;

a liposome composition entrapping a drug therein; and an insoluble polymeric substance fixed inside the container such that the liposome composition can be brought into contact with a body fluid supplied into the container.

In this apparatus, the drug entrapped in the liposome is released into the body fluid flowing in the container.

In a preferred embodiment, the insoluble polymeric substance is fixed on a surface of an insoluble support.

BRIEF DESCRIPTION OF THE DRAWINGS

FIG. 5 is a diagram of an apparatus used for performing an in vitro drug release test of the drug administering apparatus according to the present invention.

DETAILED DESCRIPTION OF THE PREFERRED EMBODIMENTS

Figure 1:
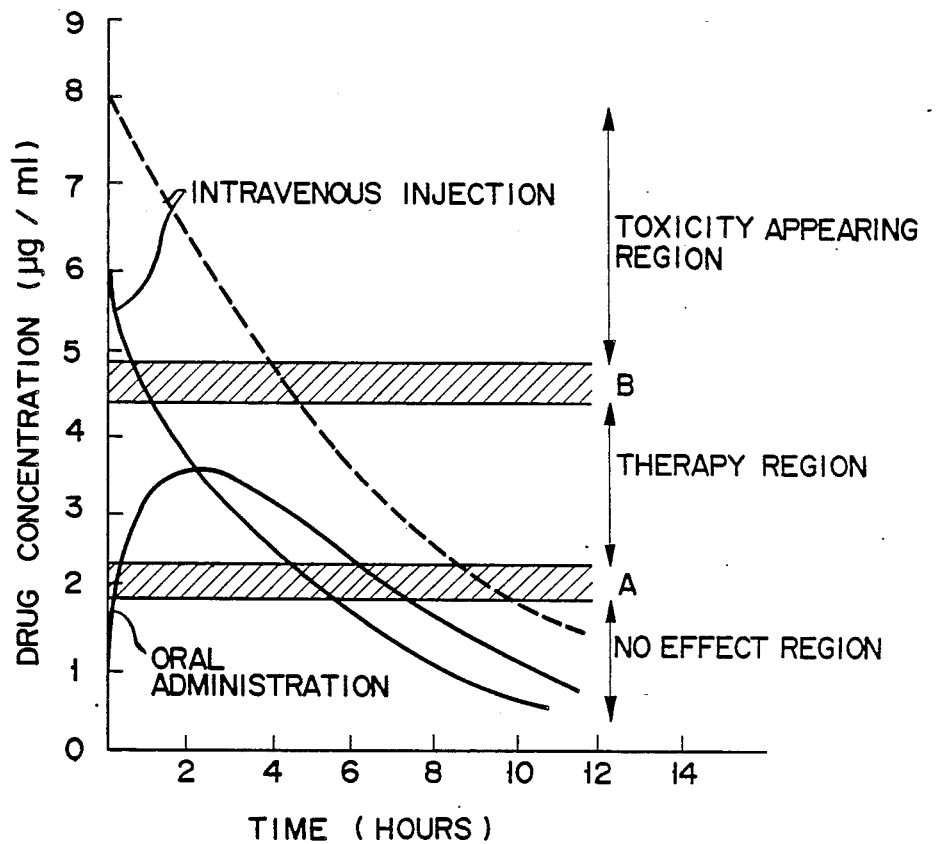
FIG. 1 is a graph showing typical changes in concentration of a drug in blood.

The present inventor has made extensive studies to develop an extracorporeal therapy column or a bioagitator which assures stability of a liposome and has an excellent sustained release property for a substance entrapped in a liposome and for the liposome itself. As a result of such studies, the following facts were ascertained. When an insoluble polymeric substance having a three-dimensional network structure (generally expressed as matrix, lattice or skeleton; to be referred to as a matrix hereinafter) in which a liposome entrapping a substance to be administered to a human body (to be referred to as an administering substance hereinafter) is held is fixed on a surface of an insoluble support filled in a container having fluid inlet and outlet ports. The matrix serves as a buffer between the body fluid and the liposome to prevent direct contact between the liposome and the body fluid and damage to the liposome membrane within a short period of time. In addition, the matrix stabilizes the liposome and effectively releases the administering substance and the liposome encapsulating the administering substance over a long period of time. When irradiation with gamma rays is performed to crosslink the polymeric substance and to form a matrix containing a three-dimensional network structure of a crosslinked polymer, the polymeric substance can be rendered insoluble while causing no damage to the liposome membrane and no toxicity. The present invention has been established based on these findings.

The insoluble support to be used in the present invention can be a hydrophilic or hydrophobic support.

The insoluble support can have any shape; granular, fibrous, hollow fiber-like, or membrane-like, etc. However, in view of the excellent permeating property of a body fluid and low damage to cells, a granular or hollow fiber support is preferably used.

Examples of granular supports to be used herein may include those made of agarose, dextran, cellulose, polyacrylamide, polyvinyl alcohol, polyvinyl pyrrolidone, polyacrylonitrile, styrene-divinyl benzene copolymer, polystyrene, acrylate ester, methacrylate ester, glass, alumina, titanium, activated carbon, and ceramic. Particularly good effects are obtained with porous polymeric granular supports, porous glass supports, or silicagel supports. Polymeric particles can be made of conventional polymers of polyamide, polyester, polyurethane, or vinyl compounds which can have a porous structure. In general, the porous granular supports preferably have a size of 0.1 mm to 5 mm, a pore size of 2 nm to 0.4 $\mu$m, and a porosity of 10 to 70%.

Hollow-fiber supports can be those made of polypropylene, cellulose acetate, methyl polymethacrylate, ethylene-vinyl acetate copolymer, polyvinyl alcohol, and glass. Particularly good effects are obtained with porous polypropylene supports, porous polyvinyl alcohol supports, or porous glass supports. In general, porous hollow fiber supports preferably have pores of a size of 2 nm to 0.4 μm and a porosity of 30 to 70%.

Examples of polymeric substances to be used herein may include polyacrylamide, polyvinyl alcohol, gelatin, or polyvinyl pyrrolidone, which have an average polymerization degree of 500 to 3,000. An aqueous solution of one or more of such polymeric substances in a concentration of 3 to 20 w/v % with or without the addition of a crosslinking agent such as methylene bisacrylamide or ethylene glycol dimethacrylate derivative is desirable.

A hydrogel is preferably used as such an aqueous solution. Hydrogels have a hydrophilic group such as a hydroxyl group, a carbonyl group or an amino group and can easily retain water. Therefore, a hydrogel has an excellent biocompatibility and is not rejected as a foreign matter by a biological organism.

Biocompatibility used herein means affinity and harmlessness upon being administered to a biological organism.

Examples of other typical hydrogels which can be used herein may include poly-(2-hydroxyethylmethacrylate), polymethacrylate, poly-(N,N-dimethylaminoethylmethacrylate), polyethylene oxide, polysaccharides, sodium alginate, collagen, and fibrin.

According to the present invention, a matrix is a substrate having a three-dimensional (stereoscopic) network structure consisting of an insoluble polymeric substance obtained by crosslinking one of the polymeric substances enumerated above. The network structure can be observed through an electron microscope. Crosslinking used herein must be interpreted in a wide sense; it includes formation of chemical bonds between linear polymers to form a network structure or copolymerization or condensation polymerization between polymers of the same type to form a network structure. As is well known, crosslinking can be performed by addition of a crosslinking agent or radiation of gamma rays or the like. A polymeric substance having a biocompatibility is preferably used. Any one of the polymeric substances enumerated above has a biocompatibility.

Formation of a matrix, i.e., treatment for rendering a polymeric substance insoluble is performed by irradiation with gamma rays at a dose of 0.5 to 4 Mrad. With this method, the polymeric substance can be rendered insoluble without damaging the liposome membrane and causing no toxicity to a biological organism. At the same time, upon formation of a matrix by this method, sterilization is also performed. Especially when a polymerization initiator such as potassium persulfate or ammonium persulfate is used, the liposome membrane may be damaged and the liposome may explode.

The liposome entrapping an administering substance within its membrane is held between lattices (minimum units constituting the network structure) of a three-dimensional network structure of the matrix. This is because the outer diameter of the liposome is larger than the size of each lattice, and the liposome cannot escape from between lattices. The liposome is particularly held at a portion of the matrix having a hydrophilic group. When the crosslinking degree is high (e.g., 6 to 80%), the liposome cannot escape from the held state in the matrix. Since the matrix serves as a buffer between the liposome and a body fluid, an excellent sustained release property of a drug is obtained. When the crosslinking degree is low (e.g., 0 to 5%), the liposome is weakly held in the matrix. Therefore, the liposome is gradually separated from the matrix, and the drug encapsulated in the liposome is released while flowing in a body fluid, also providing an excellent drug release property.

The constituting materials of a liposome to be used herein can be lipids suitable for forming liposomes, and phospholipids are preferably used as a major component.

Typical examples of phospholipids may include lecithin (phosphatidyl choline), phosphatidyl ethanolamine, phosphatidic acid, phosphatidyl serine, phosphatidyl inositol, phosphatidyl glycerol, sphingomyelin, cardiolipin, and hydrogenated products thereof.

A higher fatty acid can be added to such a liposome constituting material. A higher fatty acid having 10 to 20 carbon atoms is preferably used as the higher fatty acid. Preferable examples of higher fatty acids include unsaturated higher fatty acids having 18 to 20 carbon atoms and having 1 to 4 double bonds, such as oleic acid, linoleic acid, linolenic acid, or arachidonic acid. Oleic acid is most preferable. In general, a higher fatty acid is contained in the amount of 5 to 30% by weight based on the total weight of the liposome constituting materials.

In order to reinforce the strength of the liposome membrane, a sterol such as cholesterol or an antioxidant may be added to the liposome constituting material. Examples of such antioxidant may include a higher fatty acid ester of ascorbic acid, or tocopherol. Furthermore, in order to adjust the sustained release property of the drug or liposome, a charging agent (for imparting the same charge to the liposomes so that the liposomes repel each other and do not aggregate or fuse each other) can be added. Examples of such a charging agent may include phosphatidic acid, dicetyl phosphate, or stearylamine.

The agent for reinforcing the liposome membrane, the antioxidant, and the charging agent are added in ratios so as not to impair formation of a liposome; they are respectively contained in amounts less than 35% by weight of the total weight of the liposome constituting materials.

An administering substance to be administered the apparatus of the present invention is not particularly limited unless a selected drug impairs formation of a liposome. However, administering substances which are unstable in vitro or in vivo or which are gradually released in a human body or are preferably quickly distributed within a specific organ are preferably used. Examples of drugs in a narrow sense as such administering substances may include insulin, heparin, urokinase, ubidecarenone, methotrexate, neomycin, bleomycin, tetracycline, cytochrome, asparaginase, or cytosine arabinoside.

When an administering substance is used as a bioagitator for an immunologically competent cell, an immunosuppressive drugs such as prednisolone, thyrophosphamide, azathioprine, or actinomycin C; an immunization agent such as rentinane, rebamizol or prostaglandin; or an interferon induction agent such as lipopolysaccharide, pyran, or kanamycin is preferably used.

Drugs other than those of narrow sense as enumerated above, such as markers, plasmid, DNAs or RNAs, can be used if they are effective on being administered in a biological organism. Such an administering substance is entrapped in a liposome in an amount to provide a satisfactory effect, and the amount of administering substance is different in each type of administering substance. As can be seen from the above, drugs in narrow sense and non-drug administering substances encapsulated in a liposome and the liposome encapsulating such a drug are designated as drugs in this specification, and the present invention provides an apparatus for administering a drug, in a wide sense, to a fluid.

A liposome to be used herein is prepared by a known method. For example, at least one natural phospholipid or hydrogenated phospholipid and, if desired, a higher fatty acid, sterol, tocopherol, and a charging agent are dissolved in a suitable solvent such as chloroform or ethanol. The solvent is evaporated from the obtained homogeneous solution to prepare a lipid membrane. An aqueous solution of a drug is added to the membrane, the solution is vigorously shaken and the solution is then irradiated with ultrasonic waves to provide a drug-encapsulating liposome. The resultant liposome is washed with a physiologically acceptable solution, e.g., a physiological saline solution, if required, and is then mixed with the aqueous solution of the polymeric substance (preferably hydrogel). The mixing ratio is set such that the content of the liposome is 1 to 50 v/v %.

Figure 2:
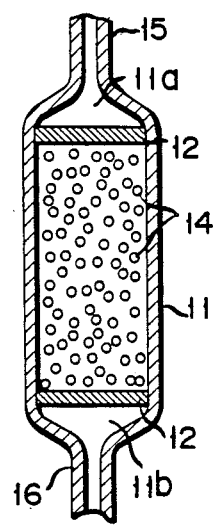
FIG. 2 is a schematic sectional view showing an embodiment of a drug administering apparatus of the present invention.

If the insoluble support is a granular support, a support having an average particle size of 0.1 to 5 mm is mixed with the liposome/hydrogel so as to coat the surface of the support particles. The mixture is dispersed in a solvent which does not damage the liposome and which is immiscible with the liposome/hydrogel, e.g., freon. The dispersion is irradiated with gamma-rays so as to render the gel insoluble. The carrier is separated from the solvent, and is washed with a physiological saline solution or the like. Thereafter, the support is filled in a column of an acrylic or polycarbonate resin or glass having at its two ends meshes of polyester, polyamide or stainless. A drug administering apparatus obtained in this manner is shown in FIG. 2.

The apparatus has a column 11 with body fluid inlet port and outlet port 11a and 11b. The column 11 further has meshes 12 at its two ends. A granular support 14 carrying the liposome thereon is filled in a space defined between the meshes 12 and the wall of the column 11. A body fluid is flowed from a line 15 into the column 11 through the inlet port 11a, is brought into contact with the liposome carried on the support 14 to be mixed with the drug released from the liposome, and is flowed back into the body through a line 16 via the outlet port 11b.

Figure 3:
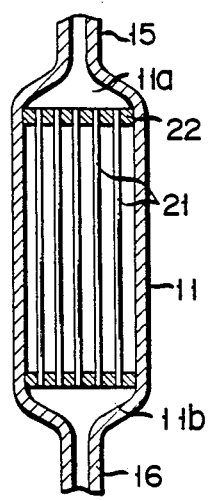
FIG. 3 is a schematic sectional view showing another embodiment of a drug administering apparatus according to the present invention.

When the insoluble support is a hollow-fiber support, 1 to 100 porous hollow fibers having a pore size of 20 Å to 0.4 μm, a length of 1 to 30 m, and a porosity of 30 to 70% are bundled into a coil. The two ends of the fiber coil are fixed with a potting material such as an epoxy resin or a polyurethane resin such that the open ends of each hollow fiber will not be closed and the coil is housed in the column. After the liposome/hydrogel is flowed into each hollow fiber, the column is left to stand for 10 to 60 minutes. The column is washed with a physiological saline solution or the like, the ends of the column are closed with a liquid-tight film or the like, and it is then irradiated with gamma-rays at a dose of 0.4 to 3 Mrad to render the gel insoluble. The residual monomer or polymer is washed with a physiological saline solution or the like. The drug administering apparatus obtained in this manner is shown in FIG. 3. The apparatus shown in FIG. 3 has a column 11 similar to that of the apparatus shown in FIG. 2, and hollow fibers 21 carrying the liposome thereon are housed therein.

Figure 4:
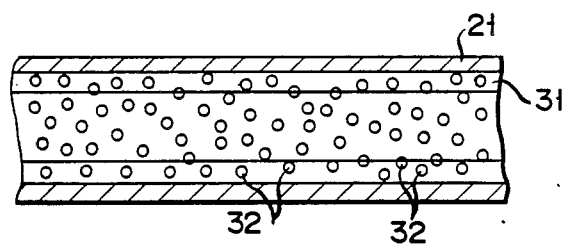
FIG. 4 is an enlarged sectional view of a hollow fiber used in the apparatus shown in FIG. 3.

The bundle of the fibers 21 is fixed and supported with potting materials 22 at the two ends of the column 11. The two ends of each hollow fiber 21 are open to an inlet port 11a and an outlet port 11b, respectively. As shown in FIG. 4, a layer 31 of an insoluble polymeric substance supporting a liposome 32 encapsulating a drug therein (liposome agent) is formed on the inner surface of each hollow fiber. A body fluid introduced into each hollow fiber 21 through a line 15 via the inlet port 11a is brought into contact with the liposome 31 in the fiber 21 and is thus mixed with the drug released from the liposome 31. The body fluid is then returned to the body through a line 16 via the outlet port 11b.

When the body fluid is circulated through a column gradually releasing a drug or liposome obtained in this manner, therapy with a drug delivery system or bioagitator can be performed.

Sustained release of a drug can also be performed by intravenous drip infusion. However, the function of the drug administering apparatus according to the present invention is different from intravenous drip infusion in that in the apparatus of the present invention a drug is brought into direct contact with blood cells instead of simply administering the drug into a body fluid such as blood. A liposome has an excellent compatibility with blood, and blood cells flowing in the apparatus of the present invention are attracted to the liposome and are brought into contact therewith for a short period of time. Therefore, the drug released from the liposome is brought into direct contact with the blood cells. This effect is particularly noticeable when the apparatus of the present invention is used as a bioagitator.

The present invention will be described with reference to an Example and a Control.

EXAMPLE

Eggyolk phosphatidyl choline, bovine sphingomyelin, cholesterol, DL-α-tocopherol, and oleic acid were dissolved in chloroform in a molar ratio of 8:2:10:0.3:1, and the resultant solution was charged in a 500 ml volume egg-plant type flask. After the solvent was evaporated with a rotary evaporator ("N-7" type evaporator available from Tokyo Rikakikai K.K.), an aqueous solution of 10,000 units of urokinase was added to the residue. After the solution obtained was mixed and agitated with a vortex mixer ("NS-8" type available from Iuchi Seieido K.K.), it was irradiated with utrasonic waves at 5° C. for 15 minutes in a water dipping type ultrasonic washer (ultrasonic oscillator "UT-302R" and ultrasonic dipping oscillator "U1-302R" available from Sharp Corp.) so as to prepare a liposome suspension.

The suspension was centrifuged at 4° C. at 150,000 G for 30 minutes with an ultra centrifuge ("70P-72" type, rotor "RP-70T" available from Hitachi Ltd.), and the obtained solid was washed twice with a physiological saline solution. The obtained pellets were suspended in a physiological saline solution and were sized to prepare a liposome suspension encapsulating urokinase. The obtained liposome had a final lipid concentration of 15 μmol/ml.

The liposome was mixed with a hydrogel solution comprising a physiological saline solution containing 15 w/v % gelatin and 1.5 w/v % N,N-methylene bisacrylamide in a mixing ratio of 1:2 by volume. The resultant liposome/hydrogel solution was flowed into polypropylene hollow fibers having a pore size of 0.55 μm and a porosity of 45% and fixed in a column after the hollow portion of each hollow fiber was wetted with ethanol.

Thus, the hollow portion of each hollow fiber was coated with the liposome/hydrogel solution. The assembly was irradiated with gamma-rays at a dose of 3 Mrad to polymerize and crosslink the solution, thereby preparing a sterilized extracorporeal circulating drug administering apparatus.

Control

In Vitro Drug Release Test of Drug Administering Apparatus

The drug administering apparatus prepared in the Example was set in an apparatus as shown in FIG. 5, and cattle blood was circulated.

Referring to FIG. 5, reference numeral 51 denotes cattle blood; 52, a blood pump; 53, the drug administering apparatus of the present invention; and 54, a blood reservoir.

The circulating blood was sampled at 30, 60, 120 and 180 minutes, respectively, after circulation was started, and the urokinase activity in the blood was examined by a synthetic substrate "S-2444" method. The obtained results are shown in FIG. 6.

Figure 6:
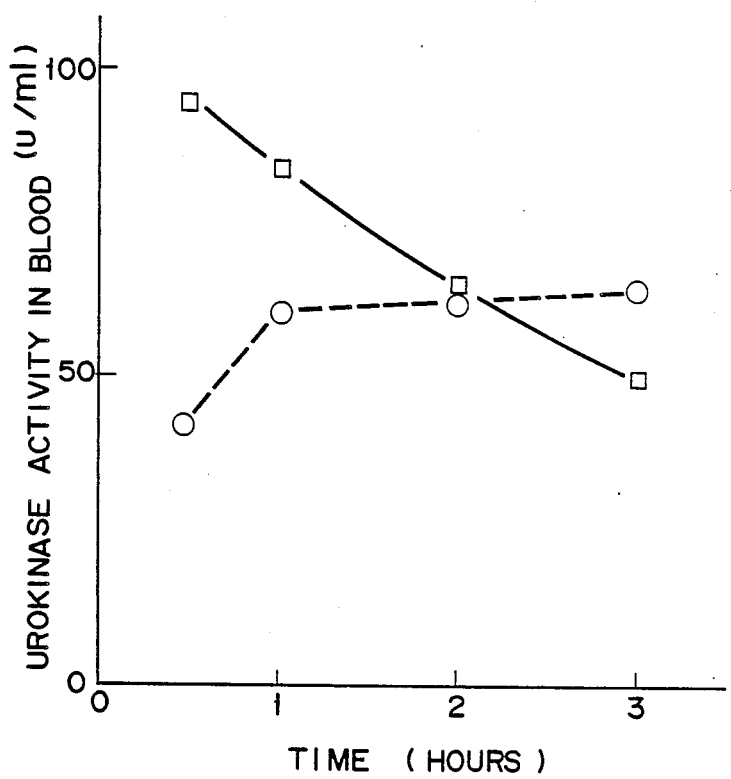
FIG. 6 is a graph showing the test result obtained using the apparatus shown in FIG. 5.

Referring to FIG. 6, the curve marked with open circles corresponds to the case of the drug administering apparatus obtained in the Example, and the curve marked with hollow squares corresponds to the case wherein the liposome in the Control was directly added to the blood and circulated.

As can be seen from FIG. 6, the drug administering apparatus of the present invention has a higher drug holding effect than the apparatus of the Control, thereby providing an excellent effect.

As described above, according to a drug administering apparatus of the present invention, a polymeric substance having a three-dimensional structure and holding a liposome agent is fixed on a surface of an insoluble substance filled in a container having fluid inlet and outlet ports. The apparatus has an excellent sustained release property of an administering drug encapsulated in the liposome and of the liposome itself, and can be used as an extracorporeal circulation therapy column capable of maintaining a stable drug effect over a long period of time or as a bioagitator for promoting or activating cell function.

When a polymeric substance having a hydrophilic group is used, it has an excellent biocompatibility and is not rejected as a foreign matter in a biological organism.

When crosslinking is performed by irradiation with gamma-rays, the matrix can be formed (the polymeric substance can be rendered insoluble) without damaging the liposome membrane and causing no toxicity to the biological organism. Irradiation with gamma-rays also has a sterilization effect.

What is claimed is:

1. A drug administering apparatus comprising:
    a container with body fluid inlet and outlet ports which communicate with each other;
    a liposome agent entrapping a drug therein; and
    an insoluble substance fixed inside said container and having said liposome agent such that said liposome agent can be brought into contact with the body fluid flowing in said container;
    said insoluble substance comprising a polymeric substance having a hydrophilic group and having been crosslinked to have a three-dimensional network structure;
    said liposome agent being held between lattices of said network structure;
    whereby said drug entrapped in said liposome agent is released into the body fluid flowing in said container.

2. An apparatus according to claim 1, wherein the polymeric substance is crosslinked by irradiation with gamma-rays.

3. An apparatus according to claim 2, wherein the polymeric substance is a hydrogel.

4. An apparatus according to claim 3, wherein the polymeric substance has a biocompatibility.

5. An apparatus according to claim 4, wherein the polymeric substance is a member selected from the group consisting of polyacrylamide, polyvinyl alcohol, gelatin, polyvinyl pyrrolidone, poly-(2-hydroxyethylmethacrylate), polymethacrylate, poly-(N,N-dimethylaminoethylmethacrylate), polyethylene oxide, polysaccharide, sodium alginate, collagen, and fibrin.

6. An apparatus according to claim 1, wherein the liposome is constituted by a phospholipid.

7. An apparatus according to claim 1, wherein the polymeric substance is fixed on an insoluble support.

8. An apparatus according to claim 7, wherein the insoluble support comprises granules filled in the container.

9. An apparatus according to claim 8, wherein the granules have an average size of 0.1 to 5 mm.

10. An apparatus according to claim 7, wherein the insoluble support comprises hollow fibers packed in the container.

11. An apparatus according to claim 10, wherein the polymeric substance is fixed on an inner surface of each of the hollow fibers.

12. A drug administering apparatus comprising:
    a container with body fluid inlet and outlet ports which communicate with each other;
    a liposome agent entrapping a drug therein; and
    an insoluble substance fixed inside said container and having said liposome agent such that said liposome agent can be brought into contact with the body fluid flowing in said container;
    said insoluble substance being crosslinked to have a three-dimensional network structure;
    said insoluble substance being obtained by irradiating a mixture of a hydrogel comprising a polymeric substance and said liposome agent with gamma rays, thereby providing said network structure and allowing said liposome agent to be held between lattices of said network structure.

13. An apparatus according to claim 12, wherein the polymeric substance is a hydrogel.

14. An apparatus according to claim 12, wherein the liposome is constituted by a phospholipid.

15. An apparatus according to claim 12, wherein the polymeric substance is fixed on an insoluble support.

16. An apparatus according to claim 12, wherein said polymeric substance is crosslinked at a crosslinking degree of 6 to 80%.

17. An apparatus according to claim 1, wherein said polymeric substance is crosslinked at a crosslinking degree of 6 to 80%.

* * * * *

UNITED STATES PATENT AND TRADEMARK OFFICE
CERTIFICATE OF CORRECTION

PATENT NO. : 4,681,582

DATED : July 21, 1987

INVENTOR(S) : Yuichi YAMAMOTO

It is certified that error appears in the above-identified patent and that said Letters Patent is hereby corrected as shown below:

On Page 1, under Foreign Application Priority Data, delete

"Jun. 13, 1984 [JP]   Japan........59-121463/1"

and kindly insert

--Jun. 13, 1984 [JP]   Japan........59-121463--.

Signed and Sealed this

First Day of December, 1987

Attest:

DONALD J. QUIGG

Attesting Officer

Commissioner of Patents and Trademarks